(12) United States Patent
Sherman et al.

(10) Patent No.: US 11,426,366 B2
(45) Date of Patent: Aug. 30, 2022

(54) COMPOSITIONS AND METHODS FOR TREATING MOTOR DISORDERS

(71) Applicant: ARIZONA BOARD OF REGENTS ON BEHALF OF THE UNIVERSITY OF ARIZONA, Tucson, AZ (US)

(72) Inventors: Scott Sherman, Tucson, AZ (US); Torsten Falk, Tucson, AZ (US); Miguel Estevez, Tucson, AZ (US)

(73) Assignee: ARIZONA BOARD OF REGENTS ON BEHALF OF THE UNIVERSSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/574,346

(22) PCT Filed: May 12, 2016

(86) PCT No.: PCT/US2016/032155
§ 371 (c)(1),
(2) Date: Nov. 15, 2017

(87) PCT Pub. No.: WO2016/186968
PCT Pub. Date: Nov. 24, 2016

(65) Prior Publication Data
US 2019/0060254 A1   Feb. 28, 2019

Related U.S. Application Data

(60) Provisional application No. 62/162,403, filed on May 15, 2015.

(51) Int. Cl.
| | |
|---|---|
| *A61P 25/26* | (2006.01) |
| *A61K 31/135* | (2006.01) |
| *A61K 31/166* | (2006.01) |
| *A61K 31/198* | (2006.01) |
| *A61K 31/454* | (2006.01) |
| *A61K 31/4545* | (2006.01) |
| *A61K 31/551* | (2006.01) |
| *A61K 31/5513* | (2006.01) |
| *A61K 31/553* | (2006.01) |
| *A61K 31/554* | (2006.01) |
| *A61K 31/5415* | (2006.01) |
| *A61K 31/4439* | (2006.01) |
| *A61P 25/16* | (2006.01) |

(52) U.S. Cl.
CPC .......... *A61K 31/135* (2013.01); *A61K 31/166* (2013.01); *A61K 31/198* (2013.01); *A61K 31/4439* (2013.01); *A61K 31/454* (2013.01); *A61K 31/4545* (2013.01); *A61K 31/5415* (2013.01); *A61K 31/551* (2013.01); *A61K 31/553* (2013.01); *A61K 31/554* (2013.01); *A61K 31/5513* (2013.01); *A61P 25/16* (2018.01)

(58) Field of Classification Search
CPC .. A61K 31/135; A61K 31/166; A61K 31/198; A61K 31/4439; A61K 31/454; A61K 31/4545; A61K 31/5415; A61K 31/551; A61K 31/5513; A61K 31/553; A61K 31/554; A61P 25/16
See application file for complete search history.

(56) References Cited

U.S. PATENT DOCUMENTS

| | | | |
|---|---|---|---|
| 5,817,699 A | 10/1998 | Flores et al. | |
| 5,866,585 A | 2/1999 | Fogel | |
| 6,248,789 B1 | 6/2001 | Weg | |
| 6,855,735 B2 | 2/2005 | Friedman | |
| 2003/0181528 A1* | 9/2003 | Friedman | A61K 31/135 514/648 |
| 2004/0248964 A1* | 12/2004 | Crooks | C07D 209/48 514/417 |
| 2005/0245617 A1* | 11/2005 | Meyerson | A61K 9/2077 514/649 |
| 2006/0189694 A1 | 8/2006 | Went et al. | |
| 2007/0042037 A1* | 2/2007 | Tagliamonte | A61K 9/1635 424/456 |
| 2012/0208851 A1 | 8/2012 | Schloss et al. | |

(Continued)

FOREIGN PATENT DOCUMENTS

| | | |
|---|---|---|
| EP | 2027854 | 2/2009 |
| WO | WO 2000016777 | 9/1999 |

(Continued)

OTHER PUBLICATIONS

Wright et al. (International Anesthesia Research Society, 108, 980-982, Mar. 2009) (Year: 2009).*

(Continued)

*Primary Examiner* — Jared Barsky
(74) *Attorney, Agent, or Firm* — Casimir Jones, S.C.; Robert A. Goetz

(57) ABSTRACT

This invention provides methods utilizing ketamine for the treatment of motor disorders and/or side effects associated with certain medications used in the treatment of motor disorders. For example, in some embodiments, methods are provided for treating side effects associated with the administration of levodopa to a subject having Parkinson's disease, by administering a dose of ketamine or a pharmaceutically acceptable salt thereof. In particular, the invention provides methods for reducing dyskinesia associated with motor disorder (e.g., Parkinson's disease) treatments, and effective doses of ketamine or a pharmaceutically acceptable salt thereof.

5 Claims, 6 Drawing Sheets

(56) References Cited

U.S. PATENT DOCUMENTS

| | | | |
|---|---|---|---|
| 2014/0120158 A1 | 1/2014 | Montefeltro | |
| 2014/0296241 A1* | 10/2014 | Wainer | A61K 31/222 514/239.5 |
| 2017/0355663 A1* | 12/2017 | Nivorozhkin | A61K 9/2027 |

FOREIGN PATENT DOCUMENTS

| | | | | |
|---|---|---|---|---|
| WO | WO 2001030346 | 10/2000 | | |
| WO | WO 2004/084952 | 10/2004 | | |
| WO | WO 2013188210 | 6/2013 | | |
| WO | WO 2014020155 | 8/2013 | | |
| WO | WO-2014020155 A1 * | 2/2014 | | A61K 9/2054 |

OTHER PUBLICATIONS

Raja, Motor dysfunction in CRPS and its treatment, 2009.*
Niesters et al., "Ketamine for Chronic Pain: Risks and Benefits," British Journal of Clinical Pharmacology, 2013.*
Correll et al., "Subanesthetic Ketamine Infusion Therapy: A Retrospective Analysis of a Novel Therapeutic Approach to Complex Regional Pain Syndrome," Pain Medicine vol. 5, No. 3, 2004.*
Kiefer et al., "Efficacy of Ketamine in Anesthetic Dosage for the Treatment of Refractory Complex Regional Pain Syndrome: An Open-Label Phase II Study," Pain Medicine vol. 9, No. 8, 2008.*
2014 PHRMA Report on Parkinson's Disease, (n.d.). Retrieved Jan. 22, 2018, fromwww.phrma.org/sites/default/files/pdf/2014-parkinsons-report.pdf.
Caixeta et al. "Ketamine alters oscillatory coupling in the hippocampus." Sci Rep 2013; 3: 2348; pp. 1-10.
Carroll, P. "Tantalizing data underscore depression-fighting potential for party drug"—Fierce Biotech May 23, 2013, from www.fiercebiotech.com/story/tantalizing-data-underscores-anti-depression-potential-party-drug/2013-05-23#ixzz32w2bPQdP.
Dekundy et al. Modulation of L-DOPA-induced abnormal involuntary movements by clinically tested compounds: further validation of the rat dyskinesia model. Behav. Brain Res 2007; 179: 76-89.
Diamond PR, et al. Ketamine infusions for treatment resistant depression: a series of 28 patients treated weekly or twice weekly in an ECT clinic. J Psychopharmacol 2014; 28: 536-544.
Feder et al. Efficacy of intravenous ketamine for treatment of chronic posttraumatic stress disorder: a randomized clinical trial. JAMA psychiatry 2014; 71: 681-688.
Ferro et al. Neuroprotective effect of ketamine/xylazine on two rat models of Parkinson's disease. Braz J Med Biol Res. Jan. 2007;40(1):89-96.
Flores et al. Differential effects of the NMDA receptor antagonist MK-801 on dopamine receptor D1- and D2-induced abnormal involuntary movements in a preclinical model. Neuroscience Letters 2014; 564: 48-52.
Hakami T, et al. NMDA receptor hypofunction leads to generalized and persistent aberrant gamma oscillations independent of hyperlocomotion and the state of consciousness. PLoS One 2009; 4: e6755.
Hammond C, Bergman H, Brown P. Pathological synchronization in Parkinson's disease: networks, models and treatments. Trends in Neurosciences 2007; 30: 357-364.
Healy, M., Drug speeds depression relief in mice and men: How does it do it? Jun. 16, 2011 Los Angeles Times.
Hille CJ, et al. Antiparkinsonian action of a delta opioid agonist in rodent and primate models of Parkinson's disease. Experimental Neurology 2001; 172: 189-198.
Hiyoshi T, et al. Differential effects of NMDA receptor antagonists at lower and higher doses on basal gamma band oscillation power in rat cortical electroencephalograms. Neuropharmacology 2014; 85: 384-396.
International Search Report & Written Opinion, International Patent Application No. PCT/US2016/032155, dated Aug. 16, 2016.
Jenkinson N, Brown P. New insights into the relationship between dopamine, beta oscillations and motor function. Trends in Neurosciences 2011; 34: 611-618.
Koprich JB, et al. The selective mu-opioid receptor antagonist ADL5510 reduces levodopa-induced dyskinesia without affecting antiparkinsonian action in MPTP-lesioned macaque model of Parkinson's disease. Mov Disord 2011; 26: 1225-1233.
Lapidus Kab, et al. A Randomized Controlled Trial of Intranasal Ketamine in Major Depressive Disorder. Biol Psychiatry 2014;76(12): 970-976.
Lee, Chong, Levodopa-induced dyskinesia: Mechanisms and management Issue: BCMJ, vol. 43, No. 4, May 2001, pp. 206-209 Articles.
Masimore B, et al. Transient striatal gamma local field potentials signal movement initiation in rats. Neuroreport 2005; 16: 2021-2024.
Murrough JW, et al. Antidepressant efficacy of ketamine in treatment-resistant major depression: A two-site randomized controlled trial. Am J Psychiatry 2013; 170: 1134-1142.
Murrough JW, et al. Rapid and longer-term antidepressant effects of repeated ketamine infusions in treatment-resistant major depression. Biol Psychiatry 2013; 74: 250-256.
Nicholson et al. "Parkinson's disease and anaesthesia" Br J Anaesth 2002; 89(6):904-16.
Nicolas MJ, et al. Ketamine-induced oscillations in the motor circuit of the rat basal ganglia. PLoS One 2011; 6: e21814.
Niesters M, Martini C, Dahan A. Ketamine for chronic pain: Risks and benefits. British J of Clinical Pharmacology 2014; 77: 357-367.
Olanow CW, et al. The scientific and clinical basis for the treatment of Parkinson disease (2009). Neurology 2009; 72: S1-S136.
Pacheco DDF, et al. Central antinociception induced by ketamine is mediated by endogenous opioids and mu- and delta-opioid receptors. Brain Research 2014; 1562: 69-75.
Pan M, et al. Deranged NMDAergic cortico-subthalamic transmission underlies parkinsonian motor deficits. J Clinical Investigation 2014; 124: 4629-4641.
Paquette M et al. MK-801 inhibits L-DOPA-induced abnormal involuntary movements only at doses that worsen parkinsonism. Neuropharmacology 2010; 58: 1002-1008.
Parkinson's disease Treatment—Michael J. Fox Foundation website Retrieved Jan. 19, 2018, www.michaeljfox.org/understanding-parkinsons/living-with-pd/topic.php?medication.
Pinault D. N-methyl d-aspartate receptor antagonists ketamine and MK-801 induce wake-related aberrant gamma oscillations in the rat neocortex. Biol Psychiatry 2008; 63: 730-735.
Razoux F, Garcia R, Léna I. Ketamine, at a dose that disrupts motor behavior and latent inhibition, enhances prefrontal cortex synaptic efficacy and glutamate release in the nucleus accumbens. Neuropsychopharmacology 2007; 32: 719-727.
Smith DJ, et al. Properties of the interaction between ketamine and opiate binding sites in vivo and in vitro. Neuropharmacology 1987; 26: 1253-1260.
Ulusoy, G. Sahin, D. Kirik. Presynaptic dopaminergic compartment determines the susceptibility to L-DOPA-induced dyskinesia in rats. Proceedings of the National Academy of Sciences, 2010; DOI: 10.1073/pnas.1003432107.
Wright JJ, Goodnight PD, Mcevoy MD. The Utility of Ketamine for the Preoperative Management of a Patient with Parkinson's Disease. Anesth and Analg 2009; 108: 980-982.
Yue X, et al. Comparative study of the neurotrophic effects elicited by VEGF-B and GDNF in preclinical in vivo models of Parkinson's disease. Neuroscience 2014; 258: 385-400.
Yue X, et al. Effects of the novel glycopeptide opioid agonist MMP-2200 in preclinical models of Parkinson's disease. Brain Research 2011; 1413: 72-83.

* cited by examiner

COMPOSITIONS AND METHODS FOR TREATING MOTOR DISORDERS

CROSS-REFERENCE TO RELATED APPLICATIONS

The present application is a Section 371 U.S. national stage entry of International Patent Application No. PCT/US2016/032155, International Filing Date May 12, 2016, which claims the benefit of expired U.S. Provisional Patent Application No. 62/162,403, filed May 15, 2015, the contents of which are incorporated by reference in their entireties.

FIELD OF THE INVENTION

This invention provides methods utilizing ketamine for the treatment of motor disorders and/or side effects associated with certain medications used in the treatment of motor disorders. For example, in some embodiments, methods are provided for treating side effects associated with the administration of levodopa (L-DOPA) to a subject having Parkinson's disease, by administering a dose of ketamine or a pharmaceutically acceptable salt thereof. In particular, the invention provides methods for reducing dyskinesia associated with motor disorder (e.g., Parkinson's disease) treatments, and effective doses of ketamine or a pharmaceutically acceptable salt thereof.

BACKGROUND OF THE INVENTION

Parkinson's disease (PD) is the $2^{nd}$ most common progressive neurodegenerative disease with the cardinal motor symptoms of tremor, rigidity, postural instability and bradykinesia (Olanow et al., 2009). These motor symptoms correspond to the loss of dopaminergic neurons with cell bodies located in the substantia nigra and axonal projections to the striatum leading to reduced dopamine (DA) levels. The most common treatment for PD consists of DA replacement therapy utilizing either the DA precursor L-DOPA or DA receptor agonists. These therapies become unsatisfactory as the disease progresses due to a variety of short-term and long-term side effects that occur with dose escalation, including the most common and debilitating side effect L-DOPA-induced dyskinesias (LID). Therefore, there is an urgent need to develop non-dopaminergic therapies. An effective treatment of LID to extend the useful lifetime of L-DOPA treatment is a critical unmet need in PD therapy.

SUMMARY

Low-dose sub-anesthetic ketamine infusion treatment has led to a long-term reduction of treatment-resistant depression and posttraumatic stress disorder (PTSD) symptom severity, as well as reduction of chronic pain states, including migraine headaches. Ketamine also is known to change oscillatory electric brain activity. One commonality between migraine headaches, depression, PTSD, Parkinson's disease (PD) and L-DOPA-induced dyskinesia (LID) is hypersynchrony of electric activity in the brain, including the basal ganglia. Therefore, experiments conducted during the course of developing embodiments for the present invention investigated the use of low-dose ketamine in the treatment of PD and LID. A long-term therapeutic effect of low-dose ketamine infusion (0.15-0.3 mg/kg/hr for 72 hrs) from five PD patient case studies (reduced dyskinesia, improved on time, and reduced depression) was shown. Additionally, ketamine (5-20 mg/kg) led to long-term dose-dependent reduction of abnormal involuntary movements in a preclinical rodent model of LID, but only when low-dose ketamine was given for 10 hours and not with a single acute low-dose ketamine injection.

Accordingly, this invention provides methods utilizing ketamine for the treatment of motor disorders and/or side effects associated with certain medications used in the treatment of motor disorders. For example, in some embodiments, methods are provided for treating side effects associated with the administration of levodopa to a subject having Parkinson's disease, by administering a dose of ketamine or a pharmaceutically acceptable salt thereof. In particular, the invention provides methods for reducing dyskinesia associated with motor disorder (e.g., Parkinson's disease) treatments, and effective doses of ketamine or a pharmaceutically acceptable salt thereof.

In certain embodiments, the present invention provides methods of preventing, attenuating, and/or treating a patient suffering from a motor disorder, comprising administering to the patient a composition comprising a dose of ketamine or a pharmaceutically acceptable salt thereof to ameliorate the symptoms of the motor disorder. In some embodiments, the methods further comprise administration of carbidopa.

In some embodiments, the ketamine is administered at a dose from about 0.15 mg/kg/hour to about 10 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 5 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 2 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 0.5 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 0.3 mg/kg/hour for at least two hours (e.g., 2, 3, 5, 10, 15, 20, 25, 30, 40, 50, 60, 70, 72, 100, etc).

In some embodiments, the ketamine is administered in a delayed release formulation. In some embodiments, the patient is human.

In some embodiments, administration of the composition comprising a dose of ketamine results in the patient experiencing chemical-induced deep brain stimulation. In some embodiments, such chemical-induced deep brain stimulation results in prevention, attenuation and/or treating of the symptoms of the motor disorder.

In some embodiments, the motor disorder is dyskinesia. In some embodiments, the motor disorder is tardive dyskinesia.

In some embodiments, the motor disorder is selected from the group consisting of Parkinson's disease, dopamine-responsive dystonia, multiple sclerosis, Huntington's disease, Creutzfeld-Jakob disease, amyotrophic lateral sclerosis, and Alzheimer's disease.

In some embodiments, the motor disorder is a side effect associated with administration of a medication to the patient. In some embodiments, the medication is a medication known to be useful for treating a neurodegenerative disorder. For example, in some embodiments, the neurodegenerative disorder is selected from the group consisting of Parkinson's disease, dopamine-responsive dystonia, multiple sclerosis, Huntington's disease, Creutzfeld-Jakob disease, amyotrophic lateral sclerosis, and Alzheimer's disease.

In some embodiments, the medication is a medication known to be useful for treating a psychotic disorder. For example, in some embodiments, the psychotic disorder is selected from the group consisting of schizophrenia, schizophreniform disorder, bipolar disorder, and schizoaffective disorder.

In some embodiments, the medication is selected from the group consisting of levodopa, haloperidol, fluphenazine, flunarizine, metoclopramide, prochlorperazine, chlorpromazine, triflupromazine, thiordazine, mesoridazine, trifluoperazine, perphenazine, perazine, chlorprothixene, droperidol, pimozide, loxapine, clozapine, quetiapine, olanzapine, risperidone, ziprasidone, Iloperidone, tiapride, sulpride, clebopride, remoxipride, veralipride, amisulpride, molindone, aripiprazole, amoxapine, flunarizine, cinnarizine, bromocriptine, pergolide, cabergoline, apomorphine, lisuride, ropinirole, pramipexole, and melatonin.

In some embodiments wherein the medication is levodopa, the ketamine administration does not reduce efficacy of the levodopa administration.

In some embodiments, the ketamine within the composition is a metabolite of ketamine. For example, in some embodiments, one or more of the following metabolites of ketamine is administered with or in lieu ketamine: R-norketamine (NK), R-dehydronorketamine (DHK), S-norketamine (NK), S-dehydronorketamine (DHK), (2R,6R)-hydroxynorketamine (HNK), and (2S,6S)-hydroxynorketamine (HNK).

In certain embodiments, the present invention provides methods of treating a human suffering from Parkinson's disease, the method comprising administering to the human a composition comprising a dose of levodopa and a composition comprising a dose of ketamine or a pharmaceutically acceptable salt thereof. In some embodiments, the methods further comprise administration of carbidopa.

In some embodiments, the ketamine is administered at a dose from about 0.15 mg/kg/hour to about 10 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 5 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 2 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 0.5 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 0.3 mg/kg/hour for at least two hours (e.g., 2, 3, 5, 10, 15, 20, 25, 30, 40, 50, 60, 70, 72, 100, etc).

In some embodiments, the ketamine is administered in a delayed release formulation. In some embodiments, the patient is human. In some embodiments, the ketamine and the levodopa are concurrently active in the human.

In some embodiments, the ketamine is administered to the human before the human develops dyskinesia associated with the levodopa administration. In some embodiments, the ketamine is administered to the human after the human develops dyskinesia associated with the levodopa administration. In some embodiments, the ketamine is administered to the human before the administration of the levodopa.

In some embodiments, the ketamine within the composition is a metabolite of ketamine. For example, in some embodiments, one or more of the following metabolites of ketamine is administered with or in lieu ketamine: R-norketamine (NK), R-dehydronorketamine (DHK), S-norketamine (NK), S-dehydronorketamine (DHK), (2R,6R)-hydroxynorketamine (HNK), and (2S,6S)-hydroxynorketamine (HNK).

In certain embodiments, the present invention provides kits comprising therapeutically effective dosages of ketamine (and/or metabolites of ketamine) and levodopa, and further comprising instructions for administering the ketamine and the levodopa to a subject suffering from dyskinesia.

DETAILED DESCRIPTION OF THE INVENTION

Figure 1:
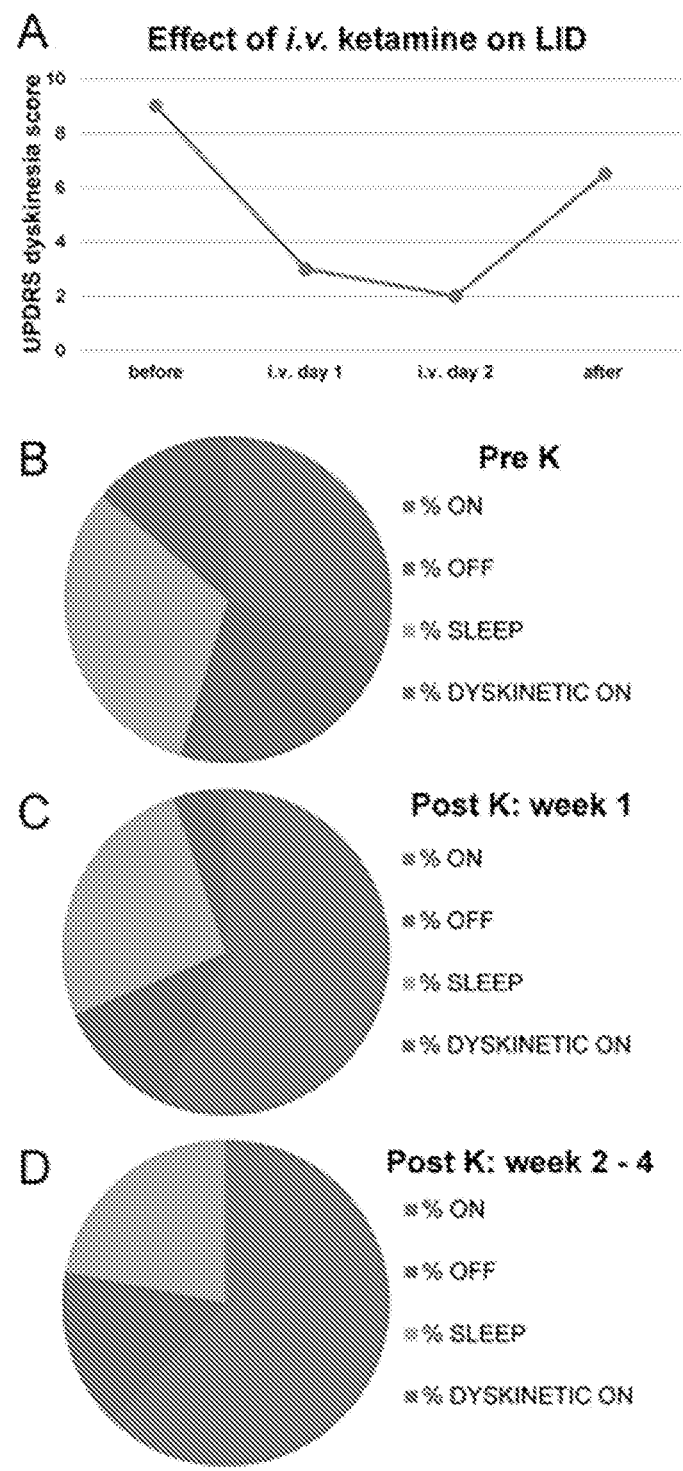
FIG. 1. UPDRS Dyskinesia score and % dyskinesia on time is reduced by low-dose ketamine infusion in case #1. The charts in (A-C) show the % time the patient spent in on, off, or dyskinetic on time, or was asleep during 24 hrs, based on the patient diary. In (A) the average of 4 pre-K days is shown and in (B) the average of the 1st week post-K. In (C) the average of weeks 2-4 post-K is depicted, and during this time the LID had completely resolved. K=72 hr low-dose ketamine-infusion. The graph (D) shows the UPDRS dyskinesia score (sum of items 32-34) before, during and after the low-dose ketamine infusion (see, Sherman S J, et al., Case Reports in Neurology 2016; 8:53-58).

Parkinson's disease (PD) is the $2^{nd}$ most common progressive neurodegenerative disease with the cardinal motor symptoms of tremor, rigidity, postural instability and bradykinesia (Olanow et al., 2009). These motor symptoms correspond to the loss of dopaminergic neurons with cell bodies located in the substantia nigra and axonal projections to the striatum leading to reduced dopamine (DA) levels. The most common treatment for PD consists of DA replacement therapy utilizing either the DA precursor L-DOPA or DA receptor agonists. These therapies become unsatisfactory as the disease progresses due to a variety of short-term and long-term side effects that occur with dose escalation, including the most common and debilitating side effect L-DOPA-induced dyskinesias (LID). Therefore, there is an urgent need to develop non-dopaminergic therapies. An effective treatment of LID to extend the useful lifetime of L-DOPA treatment is a critical unmet need in PD therapy.

Low-dose ketamine is used to treat various chronic pain syndromes, especially those that have a neuropathic component, and studies on the effect of prolonged infusion (4-14 days) show long-term analgesic effects up to 3 months following infusion (Niesters et al., 2014). Recent publications also showed that low-dose ketamine infusion paradigms are safe and well tolerated in clinical trials for treatment-resistant depression (Diamond et al., 2014; Lapidus et al., 2014; Murrough, Iosifescu, et al., 2013; Murrough, Perez, et al., 2013) and PTSD (Feder et al., 2014). Low-dose ketamine has led to a reduction of treatment-resistant depression; it also reduced PTSD symptom severity and comorbid depression. The pathophysiology of LID and motor fluctuations is uncertain, although hypotheses include an imbalance between the direct and indirect striatofugal pathways within the basal ganglia (BG), due to repeated daily administration of L-DOPA, the production of "denervation super sensitivity" of DA receptors, and as a result also hypersynchrony of electric activity and maladaptive plastic changes in the brain, including in the BG, which is a commonality between LID, depression and PTSD.

Based on this information it was hypothesized that use of low-dose ketamine infusions might help with treatment of PD, especially LID. Therefore, low-dose-ketamine infusions were investigated in five PD patient case studies and the standard preclinical LID model.

Experiments conducted during the course of developing embodiments for the present invention investigated the use of low-dose ketamine in the treatment of PD and LID. A long-term therapeutic effect of low-dose ketamine infusion (0.15-0.3 mg/kg/hr for 72 hrs) from five PD patient case studies (reduced dyskinesia, improved on time, and reduced depression) was shown. Additionally, in a preclinical rodent model of LID, ketamine (5-20 mg/kg) led to long-term dose-dependent reduction of abnormal involuntary movements, only when low-dose ketamine was given for 10 hours and not with a single acute low-dose ketamine injection.

The utility of ketamine for preoperative management with Parkinson's Disease patients has been described (see, e.g., Wright, et al., 2009), wherein an acute effect of ketamine on levodopa-induced dyskinesia (LID) is detected. The technology described herein, however, is not derivative of this unsurprising and expected observation. Indeed, an acute effect of ketamine and other NMDA-blocking drugs on LID is well-known. For example, the NMDA blocking drug, amantadine is in routine clinical use to acutely treat LID. The acute effect of ketamine, described by Wright et al., is only useful in the proscribed setting of anesthesia care.

In contrast, the technology described herein pertains to the use of a particular and unique treatment protocol that induces long-lasting or permanent beneficial effects to reduce or eliminate LID. Such technology describes a separate line of reasoning built on separate experimental observations and clinical practice. Unlike the use of ketamine for acute effects, the treatment regimen described herein involves continuous infusion of low-dose ketamine which cannot be attributed to the mere presence of an NMDA-blocking drug producing a simple pharmacological effect. Blockade of NMDA receptors alone as theorized by Wright et al. does not lead to an extended beneficial effect. Instead, as shown by the experiments described herein, long-lasting effects are dependent on additional properties of ketamine acting though other neurological mechanisms such as the induction of specific changes in the oscillatory activity of brain regions affected by Parkinson disease.

Additionally, the experimental findings described herein show that low-dose-ketamine infusion also has a preventative effect by reducing the severity of LID when used during the period of developing LID.

Accordingly, this invention encompasses preventing, attenuating, and/or treating a motor disorder and/or side effects related to the treatment of a motor disorder.

For example, this invention encompasses use of ketamine and derivatives thereof (e.g., metabolites of ketamine) for preventing, attenuating, and/or treating a motor disorder including, but not limited to, Parkinson's disease, dopamine-responsive dystonia, multiple sclerosis, Huntington's disease, Creutzfeld-Jakob disease, amyotrophic lateral sclerosis, and Alzheimer's disease.

For example, this invention encompasses use of ketamine and derivatives thereof for preventing, attenuating, and/or treating side effects related to the treatment of a motor disorder (e.g., side effects or movement disorders that are associated with dopamine-related drugs) (e.g., L-DOPA-induced dyskinesia (LID)). In some embodiments, the use of ketamine and/or derivatives thereof (e.g., metabolites of ketamine) permits the simultaneous use of a higher than normal dosage of L-DOPA or other dopamine-related drug while preventing, attenuating, and/or treating side effects related to the treatment of a motor disorder (e.g., side effects or movement disorders that are associated with dopamine-related drugs) (e.g., L-DOPA-induced dyskinesia (LID)).

For example, this invention encompasses use of ketamine and derivatives thereof (e.g., metabolites of ketamine) for preventing, attenuating, and/or treating side effects related to the treatment of a psychotic disorder (e.g., tardive dyskinesia related to use of neuroleptic medication based treatment of, for example, schizophrenia, schizophreniform disorder, bipolar disorder, and schizoaffective disorder) (e.g., treatment with a neuroleptic medication such as haloperidol).

For example, this invention encompasses use of ketamine and derivatives thereof (e.g., metabolites of ketamine) for preventing, attenuating, and/or treating side effects related to the use of medications such as, for example, levodopa, haloperidol, fluphenazine, flunarizine, metoclopramide, prochlorperazine, chlorpromazine, trifluopromazine, thioridazine, mesoridazine, trifluoperazine, perphenazine, perazine, chlorprothixene, droperidol, pimozide, loxapine, clozapine, quetiapine, olanzapine, risperidone, ziprasidone, lloperidone, tiapride, sulpride, clebopride, remoxipride, veralipride, amisulpride, molindone, aripiprazole, amoxapine, flunarizine, cinnarizine, bromocriptine, pergolide, cabergoline, apomorphine, lisuride, ropinirole, pramipexole, and melatonin.

For example, this invention encompasses use of ketamine and derivatives thereof (e.g., metabolites of ketamine) for preventing, attenuating, and/or treating motor disorder side effects in a patient with PD, including but not limited to dyskinesia or other motor disorder side effects or movement disorders that are associated with dopamine-related drugs.

Such methods of the invention comprises, for example, administering to a patient in need thereof a therapeutic dose of ketamine and/or a derivative thereof (e.g., a pharmaceutically acceptable salt).

Optionally in combination with a therapeutic dose of ketamine and/or a derivative thereof (e.g., metabolites of ketamine), the invention encompasses administering to the patient in need thereof a compound that targets the same, a similar, or a different drug pathway, one that is useful in treating L-DOPA-induced dyskinesia (LID) or other movement disorders or motor disorder side effects associated with dopamine-related drugs, one that is useful in treating PD, or one that is useful for treating both LID or other movement disorders, or motor disorder side effects associated with dopamine-related drugs and PD. This additional compound may also be useful such that the effective dose of L-DOPA or other dopamine-related drug that is necessary to treat PD is reduced. In some embodiments, the invention contemplates administering to the patient in need thereof L-DOPA, in addition to a compound that targets the same, a similar, or a different drug pathway, one that is useful in treating L-DOPA-induced dyskinesia (LID), one that is useful in treating PD, or one that is useful for treating both LID or other movement disorders or motor disorder side effects associated with dopamine-related drugs and PD.

The dopamine-related drugs encompassed by the invention include drugs that increase the activity of the dopamine receptor, including dopamine agonists and partial agonists, whether acting directly or indirectly, as well as dopamine precursors, such as L-DOPA. In a preferred embodiment, the dopamine-related drug treatment is L-DOPA therapy.

In some embodiments, the dopamine-related drug may be a dopamine receptor agonist, including, but not limited to bromocriptine, pergolide, cabergoline, apomorphine, and lisuride, or a non-ergoline dopamine agonist, including, but not limited to ropinirole or pramipexole.

In yet other embodiments, the methods of the invention encompass preventing, attenuating, and/or treating any of the motor disorder side effects described herein, associated with a combination of dopamine-related drug treatments, such as a combination of a dopamine precursors, a combination of dopamine agonists or partial agonists, and a combination of one or more dopamine precursors and one or more dopamine agonists or partial agonists.

Dopamine precursors such as L-DOPA are often administered with a DOPA decarboxylase inhibitor (DDCI) (also known as aromatic L-amino acid decarboxylase inhibitors (AAADI)). Non-limiting examples of such compounds contemplated by the invention include benserazide (Madopar, Prolopa, Modopar, Madopark, Neodopasol, and EC-Doparyl); carbidopa (Lodosyn, Sinemet, Parcopa, and Atamet); and Methyldopa (Aldomet, Aldoril, Dopamet, and Dopegyt).

In addition to DDCIs, L-DOPA or other dopamine precursors are also often administered with compounds that inhibit the action of catechol-O-methyl transferase (COMT inhibitors). Non-limiting examples of COMT inhibitors contemplated by the invention are entacapone, tolcapone, and nitecapone.

The methods of the invention, therefore, encompass preventing, attenuating, and/or treating any of the motor disorder side effects described herein, associated with L-DOPA treatment or treatment with another dopamine-related drug, L-DOPA treatment or other dopamine-related drug treatment in combination with DDCI (AAADI) treatment, L-DOPA treatment or other dopamine-related drug treatment in combination with COMT inhibitors, and L-DOPA treatment or other dopamine-related drug treatment in combination with DDCI (AAADAI) treatment and COMT inhibitors.

In one embodiment, the methods of the invention encompass preventing, attenuating, and/or treating any of the motor disorder side effects described herein, associated with administering the combination of carbidopa and levodopa. In one embodiment, the combination of carbidopa and levodopa is administered as Rytary.

In one embodiment, the methods of the invention encompass preventing, attenuating, and/or treating any of the motor disorder side effects described herein, associated with administering the combination of carbidopa, levodopa, and entacapone. In one embodiment, the combination of carbidopa, levodopa, and entacapone is administered as Stalevo.

In another embodiment, the methods of the invention encompass preventing, attenuating, and/or treating PD itself, including the movement disorders associated with PD.

In one embodiment, this invention provides a method of prevention, attenuation, and/or treatment of motor disorder side effects, including but not limited to dyskinesia, that are associated with L-DOPA therapy or other dopamine-related drugs in Parkinson's patients comprising administering to a patient in need thereof a therapeutic dose of ketamine.

In one preferred embodiment, the invention provides a method of preventing, attenuating, and/or treating Parkinson's disease, comprising administering to a patient in need thereof a dopamine-related drug and most preferably, L-DOPA, in combination with a therapeutic dose of ketamine or a pharmaceutically acceptable acid addition salt thereof.

In some embodiments, the invention provides methods for treating one or more symptoms of Parkinson's disease. Examples of such symptoms include but are not limited to dyskinesia, hyperkinesia, speech changes, loss of facial expression, cognitive dysfunction, mood swings, emotional lability, euphoria, bipolar syndrome, anxiety, aphasia, dysphasia, or disturbances, dementia or confusion, depression, fear, anxiety, memory difficulties, slowed thinking, sexual dysfunction, fatigue, aching, and loss of energy.

For all the conditions described herein, one of ordinary skill in the art will appreciate how to determine the presence or absence of characteristic symptoms and also how to diagnose these conditions. A number of criteria for diagnosing disease are useful for characterizing these conditions such as for example, NINCDS-ADRDA criteria, the ICD-IO criteria, and/or the DSM-IV criteria. Other manuals useful in diagnosing the conditions described herein include for example, but are not limited to Oppenheimer's Diagnostic Neuropathology: A Practice Manual; Harrison's Principles of Internal Medicine (Ed. Kasper et al, 16th Ed. 2005 McGraw Hill, Columbus, Ohio); Goetz: Textbook of Clinical Neurology (Eds. Goetz, Pappert, 2nd Ed. 2003, W.B. Saunders, Philadelphia, Pa.). One of ordinary skill will be aware of other such manuals routinely used in the art to diagnose these conditions.

Ketamine

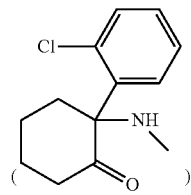 [SMILES: CNC1(c2ccccc2Cl)CCCCC1=O]

((RS)-2-(2-Chlorophenyl)-2-(methylamino)cyclohexanone) is particularly preferred for use with this invention, including pharmaceutically acceptable salts thereof. This invention also includes the use of prodrugs of the compounds of the formulas provided, specifically derivatives of the compounds of the formulas that are inactive but are converted to an active form in the body following administration.

In one embodiment, ketamine and/or a related compound(s) is administered in combination with one or more additional compound(s). The additional compound(s) may have actions that are similar to, synergistic to, or different than ketamine and/or its related compound(s).

In one embodiment, ketamine and/or a related compound(s) is administered optionally in combination with one or more additional compound(s) listed above for prevention, attenuation, and/or treatment of dyskinesia or other motor disorder side effect that is associated with L-DOPA therapy or other dopamine-related drugs in Parkinson's patients. In another embodiment, ketamine and/or a related compound(s) is administered optionally in combination with one or more additional compound(s) listed above for prevention, attenuation, and/or treatment of PD.

In yet another embodiment, L-DOPA is administered to a PD patient in need thereof, and following this administration, by the methods described herein, ketamine and/or a related compound(s) is administered optionally in combination with one or more additional compound(s) listed above for prevention, attenuation, and/or treatment of dyskinesia that is associated with L-DOPA therapy. In yet another embodiment, L-DOPA is administered to a PD patient in need thereof following the administration of ketamine and/or a related compound(s) optionally in combination with one or more additional compound(s) listed above for prevention, attenuation, and/or treatment of dyskinesia that is associated with L-DOPA therapy.

In yet another embodiment, L-DOPA is administered to a PD patient in need thereof, and following this administration, by the methods described herein, ketamine and/or a related compound(s) is administered after the development of motor side effects, optionally in combination with one or more additional compound(s) listed above for prevention, attenuation, and/or treatment of dyskinesia that is associated with L-DOPA therapy.

In yet another embodiment, L-DOPA is administered to a PD patient in need thereof, and following this administration, by the methods described herein, ketamine and/or a related compound(s) is administered prior to the development of motor side effects, optionally in combination with one or more additional compound(s) listed above for prevention, attenuation, and/or treatment of dyskinesia that is associated with L-DOPA therapy.

In one embodiment, ketamine and/or a related compound(s) is administered in combination with at least one NMDA receptor antagonist. In another embodiment, ketamine and/or a related compound(s) is administered in combination with remacemide. In yet another embodiment, ketamine and/or a related compound(s) is administered in combination with amantadine.

The doses of the compounds used in treating the disorders described herein in accordance with this invention will vary in the usual way with the seriousness of the disorder, the weight, and metabolic health of the individual in need of treatment. The preferred initial doses for the general patient population will be determined by routine dose-ranging studies, as are conducted, for example, during clinical trials. Therapeutically effective doses for individual patients may be determined, by titrating the amount of drug given to the individual to arrive at the desired therapeutic or prophylactic effect, while minimizing side effects.

Useful doses of ketamine are from about 0.25 to about 500 mg/day, from about 0.25 to about 450 mg/day, from about 0.25 to about 300 mg/day, from about 0.25 to about 290 mg/day, from about 0.25 to about 280 mg/day, from about 0.25 to about 265 mg/day, from about 0.25 to about 262 mg/day, from about 0.25 to about 255 mg/day, from about 0.25 to about 250 mg/day, from about 0.25 to about 245 mg/day, from about 0.25 to about 240 mg/day, from about 0.25 to about 225 mg/day, from about 0.25 to about 220 mg/day, from about 0.25 to about 200 mg/day, from about 0.25 to about 180 mg/day, from about 0.25 to about 175 mg/day, from about 0.25 to about 150 mg/day, from about 0.25 to about 149 mg/day, from about 0.25 to about 140 mg/day, from about 0.25 to about 125 mg/day, from about 0.25 to about 115 mg/day, from about 0.25 to about 110 mg/day, from about 0.25 to about 105 mg/day, from about 0.25 to about 100 mg/day, from about 0.25 to about 95 mg/day, from about 0.25 to about 90 mg/day, from about 0.25 to about 76 mg/day, from about 0.25 to about 70 mg/day, from about 0.25 to about 60 mg/day, from about 0.25 to about 55 mg/day, from about 0.25 to about 50 mg/day, from about 0.25 to about 48 mg/day, from about 0.25 to about 40 mg/day, from about 0.25 to about 30 mg/day, from about 0.25 to about 25 mg/day, from about 0.25 to about 20 mg/day, from about 0.25 to about 10 mg/day, from about 2.5 to about 10 mg/day, from about 2.5 to about 7.5 mg/day. In some embodiments, the dose of ketamine and/or related compounds is from about 2.5 to about 150 mg/day. In some embodiments, the dose of ketamine and/or related compounds is from about 2.5 to about 100 mg/day. In some embodiments, the daily dose of ketamine and/or related compounds is about 1 mg, 2 mg, 2.5 mg, 5 mg, 7 mg, 7.5 mg, 9 mg, 10 mg, 12 mg, 15 mg, 17 mg, 19 mg, 20 mg, 25 mg, 50 mg, 55 mg, 60 mg, 75 mg, 85 mg, 100 mg, 110 mg, 125 mg, 150 mg, 180 mg, 200 mg, 225 mg, 250 mg, 280 mg, 290 mg, 300 mg, 310 mg, 325 mg, 350 mg, 375 mg, 380 mg, 390 mg, 399 mg, 400 mg, 415 mg, 425 mg, 450 mg, 475 mg, 480 mg, 490 mg, 500 mg. Administration schedules may also be altered to achieve a therapeutically effective concentration of compound to treat the disorder or symptoms described herein. Ketamine administration schedules and dosages may also vary depending on the type of delivery (e.g., intranasal, transdermal, oral, intravenous, etc.).

In some embodiments, ketamine and/or related compounds may be administered once per day, hourly, twice per day, thrice per day, 4 times per day, 5 times per day, 7 times per day or 10 times per day. In a preferred embodiment, ketamine is administered once per day. Often the dosage is divided equally throughout the day, however in some embodiments to treat certain disorders or symptoms, it may be useful to bias the dosage administration schedule so that most of the daily treatment is administered at the beginning half of the day. In some embodiments, about 50%, 60%, 70% or 80% of the dosage is administered in the first half of the day. In other embodiments, it may be more appropriate to administer most of the dosage in the latter half of the day so that about 50%, 60%, 70% or 80% of the dosage is administered in the latter half of the day.

In some embodiments, the ketamine is administered at a dose from about 0.15 mg/kg/hour to about 10 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 5 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 2 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 0.5 mg/kg/hour for at least two hours (e.g., 2, 3, 5, 10, 15, 20, 25, 30, 40, 50, 60, 70, 72, 100, etc). In some embodiments, the ketamine is administered at a dose from about 0.15 mg/kg/hour to about 0.3 mg/kg/hour for at least two hours (e.g., 2, 3, 5, 10, 15, 20, 25, 30, 40, 50, 60, 70, 72, 100, etc).

Administration of the compounds of this invention may be by any method used for administering therapeutics, such as for example, oral, parenteral, intravenous, intramuscular, subcutaneous, intranasal, rectal, or topical administration, such as through the use of a transdermal patch.

It will be appreciated by one of ordinary skill in the art that age of the patient with the conditions described herein may respond to treatment at different degrees depending on factors such as dosage or administration or the presence of other factors or co-morbid conditions. Therefore, one of ordinary skill in the art will appreciate that the methods described herein may be directed to a particular age group.

In addition to comprising the therapeutic compounds for use in this invention, especially ketamine or pharmaceutically acceptable salts or pro-drug thereof, the pharmaceutical compositions for use with this invention may also comprise a pharmaceutically acceptable carrier. Such carriers may comprise additives, such as preservatives, excipients, fillers, wetting agents, binders, disintegrants, buffers may also be present in the compositions of the invention. Suitable additives may be, for example magnesium and calcium carbonates, carboxymethylcellulose, starches, sugars, gums, magnesium or calcium stearate, coloring or flavoring agents, and the like. There exists a wide variety of pharmaceutically acceptable additives for pharmaceutical dosage forms, and selection of appropriate additives is a routine matter for those skilled in art of pharmaceutical formulation.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose. Unit dose forms for oral administration may be tablets, capsules, and the like, and may contain conventional excipients such as binding agents, for example syrup, acacia, gelatin, sorbitol, tragacanth, or polyvinylpyrrolidone; and carriers or fillers, for example lactose, sugar, maize-starch, calcium phosphate, sorbitol or glycine. Additives may include disintegrants, for example starch, polyvinylpyrrolidone, sodium starch glycolate or microcrystalline cellulose; preservatives, and pharmaceutically acceptable wetting agents such as sodium lauryl sulphate.

In addition to unit dose forms, multi-dosage forms are also contemplated to be within the scope of the invention. Modified or controlled release dosage forms are contemplated for use in the invention, including, but not limited to sustained release dosage forms, extended release dosage forms, delayed release dosage forms, and pulsatile release dosage forms.

Suitable polymers for use in the controlled release formulations of the present invention include, but are not limited to uncrosslinked, linear polymers including cellulosic polymers, preferably hydroxyethyl cellulose, sodium carboxymethyl cellulose, hydroxypropylmethyl cellulose and hydroxypropyl cellulose, microcrystalline cellulose, methyl cellulose, and ethyl cellulose, and combinations thereof; covalently crosslinked insoluble polymers such as high molecular weight crosslinked homopolymers and copolymers of (meth) acrylic acid including carbopol resins, or mixtures of these uncrosslinked and covalently crosslinked polymers. Additionally suitable polymers include acrylic acid, methacrylic acid, methyl acrylate, ammonio methylacrylate, ethyl acrylate, methyl methacrylate and/or ethyl methacrylate, vinyl polymers and copolymers such as polyvinyl pyrrolidone, polyvinyl acetate, polyvinylacetate phthalate, vinylacetate crotonic acid copolymer, and ethylene-vinyl acetate copolymers, to name a few. Various combinations of two or more of the above polymers are also contemplated for use in the dosage forms of the invention.

Delayed release compositions may be prepared, for example, by employing slow release coatings, micro encapsulation, and/or slowly dissolving polymers.

The solid oral compositions may be prepared by conventional methods of blending, filling, tabletting or the like. Repeated blending operations may be used to distribute the active agent throughout those compositions employing large quantities of fillers. Such operations are conventional in the art. The tablets may be coated according to methods well known in normal pharmaceutical practice, for example with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, and hydrogenated edible fats; emulsifying agents, for example lecithin, sorbitan monooleate, or acacia; non-aqueous vehicles (which may include edible oils), for example almond oil or fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions, the compound can be dissolved in water or saline for injection and filter sterilized before filling into a suitable vial or ampoule and sealing. Advantageously, additives such as a local anesthetic, preservative and buffering agent can be dissolved in the vehicle. Suitable buffering agents are, for example, phosphate and citrate salts. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by conventional means, for example by exposure to radiation or ethylene oxide, before being suspended in the sterile vehicle. Advantageously, a surfactant or wetting agent is included in the composition to facilitate uniform distribution of the compound.

The ketamine and, optionally, at least one additional compound may be provided in a kit. In one embodiment, a kit may comprise at least ketamine and at least one additional compound. In one embodiment, a kit may comprise at least ketamine, L-DOPA or other dopamine-related drug, and optionally at least one additional compound. In a further embodiment, a kit as in any one of the previously described may also include instructions for administration of the compounds. In one embodiment, the kit is intended for use by a subject having PD.

EXPERIMENTAL

Example I

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Materials and Methods

Study Approval:

The human case report study was approved by the Institutional Review Board, University of Arizona and written informed consent was received from participants. All animals were treated as approved by the Institutional Animal Care and Use Committee, University of Arizona and in accordance with the NIH Guidelines for the Care and Use of Laboratory Animals. Both the number of animals used and their suffering were minimized.

Animals:

Male Sprague-Dawley rats (250 g; Harlan Laboratories, Indianapolis, Ind.) were used and housed in a temperature and humidity controlled room with 12 hr reversed light/dark cycles with food and water available ad libitum.

Unilateral 6-hydroxydopamine (6-OHDA)-Lesion Rat PD Model:

20 µg 6-OHDA hydrochloride (Sigma-Aldrich, USA) were injected into the medial forebrain bundle, as published (Flores et al., 2014).

Induction of LID in Unilaterally-Lesioned Rats:

1) Amphetamine-induced ipsiversive rotations were recorded, as published (Yue et al., 2011), to select animals. Mean ipsiversive rotations/min±SEM: cohort #1=5.5±0.7 (n=5); cohort #2=6.9±1.1 (n=10). 2) Rats were treated daily for 3 weeks with L-DOPA±14 mg/kg benserazide; both i.p.; Sigma-Aldrich): cohort #1 (severe dyskinesia): 7 mg/kg L-DOPA; cohort #2 (moderate dyskinesia): 5 mg/kg L-DOPA.

Behavioral Analysis in the LID Rat Model:

L-DOPA-induced AIMs were scored by an experimentally blinded investigator, as published (Flores et al., 2014). At the end of the experiment the rats were euthanized, and 30 minutes prior both cohorts were divided into 2 groups receiving either a 20 mg/kg ketamine or saline injection (i.p.).

Measurement of Dopamine Content:

Coronal brain slices were collected and 2 mm steel biopsy punches were used to sample striatal tissue. Samples from left and right hemispheres were collected and immediately flash frozen on an aluminum pan at −70° C., as published (Flores et al., 2014). Samples massed at 2.5±0.5 mg and were then homogenized in dilute perchloric acid. High performance liquid chromatography with electrochemical detection (HPLC-EC) was used to quantify DA.

Western Analysis of Tyrosine Hydroxylase (TH) Content:

After the tissue punch, described above, the remaining striata from left and right hemispheres were immediately flash frozen and stored at −70° C. Total protein was prepared and semi-quantitative western analysis was conducted as described (Flores et al., 2014; Yue et al., 2014) with 3 modifications. 30 μg of protein/sample was loaded and analyzed on the same blot. Secondary antibody dilution for β-actin: 1:10,000. Images were analyzed with the G:Box XR5 Chemi system (Syngene, Frederick, Md.) using GeneSys v. 1.4.0.0.

Data Analysis:

Statistical analysis was performed using GraphPad Prism 5.1 software (GraphPad Software, La Jolla, Calif.), Origin 9.0 (OriginLab Corporation, Northampton, Mass.) and Microsoft Excel 2013. The null hypothesis was rejected when $p<0.05$.

Results

We report on five cases of low-dose ketamine infusion in patients with PD identified by a retrospective chart review (Table 1). Ketamine was indicated for a variety of co-morbid conditions. The level of documentation of PD and LID symptoms pre and post-infusion was variable, but in many cases included standardized clinical rating scales collected by Movement Disorder specialists. Overall, the case reports indicate excellent tolerability and safety of ketamine in this group of patients. Patients were treated in the intensive care unit using a protocol developed by one of the authors (ME) for treatment of intractable headache that specified titration of ketamine to a target rate of 0.15 mg/kg/hr for a 72 hr period. Variations in the dosing are shown in Table 1.

lumbar degenerative disk disease which was exacerbated by often severe and violent dyskinesia. During admission, no adjustments were made to the dosages of carbidopa/L-DOPA or other medications, yet his dyskinesia improved markedly during and after the infusion. He was free of dyskinesia at the time of a second infusion 3 years later despite an increase in L-DOPA dose. At that time the patient was noted to have severe tremor, which resolved acutely during the infusion. Unlike the dyskinesia, the beneficial effect on tremor was short-lived since the tremor had returned at a follow-up visit 3 weeks later. The patient continues to be followed by one of the investigators (SJS) and has remained free of dyskinesia.

Similarly, in case #2 there was a dramatic reduction in dyskinesia as reported by one of the authors (ME) though less quantitative data is available from chart review. Notably, prior amantadine (200 mg daily) treatment had failed to improve his LID.

Case #3 was a patient with severe back pain, depression, and advanced PD. Ketamine dramatically improved the patient's depression, pain, and acutely improved his motor symptoms. The patient had significant comorbid medical problems including reduced cardiac ejection fraction, and arrhythmia. Though dyskinesia was not the most prominent feature of his motor symptomatology, it is notable that it completely subsided following the infusion, and that there was acute improvement in other aspects of the motor exam during the infusion. His depression was dramatically improved (Table 1, patient was suicidal before infusion and only mildly depressed on subsequent follow-up visits, followed by SJS). This case supports the safety and feasibility of using low-dose ketamine even in patients of advanced age and with comorbid conditions.

Cases #4 and 5 had intractable headache and relatively early-onset PD, treated with subthalamic nucleus (STN) deep brain stimulation (DBS) which had previously resolved their dyskinesia and motor fluctuations. In case #4 the headache occurred after DBS placement and may have been related to hardware placement, in case #5 the headache preceded DBS placement. The headache was improved in

TABLE 1

Patient details.

| case # | Demographics | | | Hohn Yahr | L-DOPA Equiv. | Ketamine infusion | | | | Clinical effects of ketamine | | | | | | side effects RASS |
|---|---|---|---|---|---|---|---|---|---|---|---|---|---|---|---|---|
| | | | Disease Duration | | | indication | starting dose | max dose | duration (hours) | average dose | UPORS pt 3 | | | pain | | |
| | age | sex | | | | | | | | | before | during | after | before | during | after | |
| 1 | 64 | m | 20 | 3 | 2400 | back pain | 0.06 | 0.3 | 60 | nd | nd | nd | nd | nd | nd | nd | nd |
| 1-B | 67 | m | 23 | 3 | 3208 | back pain | 0.1 | 0.3 | 67 | 0.24 | 48 | 18 | 40 | 8 | 1 | 1 | 0.20 |
| 2 | 62 | m | >10 | 3 | 2150 | painful dyskinesia | 0.15 | 0.15 | 72 | 0.15 | nd | nd | nd | nd | nd | nd | nd |
| 3 | 84 | m | 12 | 3 | 1971 | back pain | 0.05 | 0.15 | 55 | 0.09 | 40.5 | nd | 28 | 8 | 0.73 | 0 | 0.14 |
| 4 | 46 | f | 6 | 2.5 | 400 | headache | 0.05 | 0.15 | 96 | 0.59 | nd | nd | nd | 10 | 5.5 | 5 | 0.42 |
| 5 | 54 | f | 5 | 2.5 | 400 | headache | 0.05 | 0.15 | 72 | 0.12 | nd | nd | nd | nd | nd | nd | nd | nd: not determined:
UPORS, unified Parkinson's disease rating scale:
0.10 Pain Scale Assessment:
RASS Richmond Agilation Sedation Scale Case #1 demonstrates a remarkable observation of resolution of LID in a patient with long-standing PD who routinely completed all-day diaries of his motor fluctuations, and underwent close clinical observation (FIG. 1 A, B). This patient was treated for intractable back pain due to severe case #4, but in case #5 the patient requested the infusion be aborted due to non-efficacy and non-specific side effects. These cases are included for completeness of documentation and safety data but there was little effect on motor symptoms. Though in case #4, the intensity of DBS stimulation was reduced by 0.3 volts bilaterally with improvement of stimulation induced dysarthria without loss of motor benefit.

Figure 2:
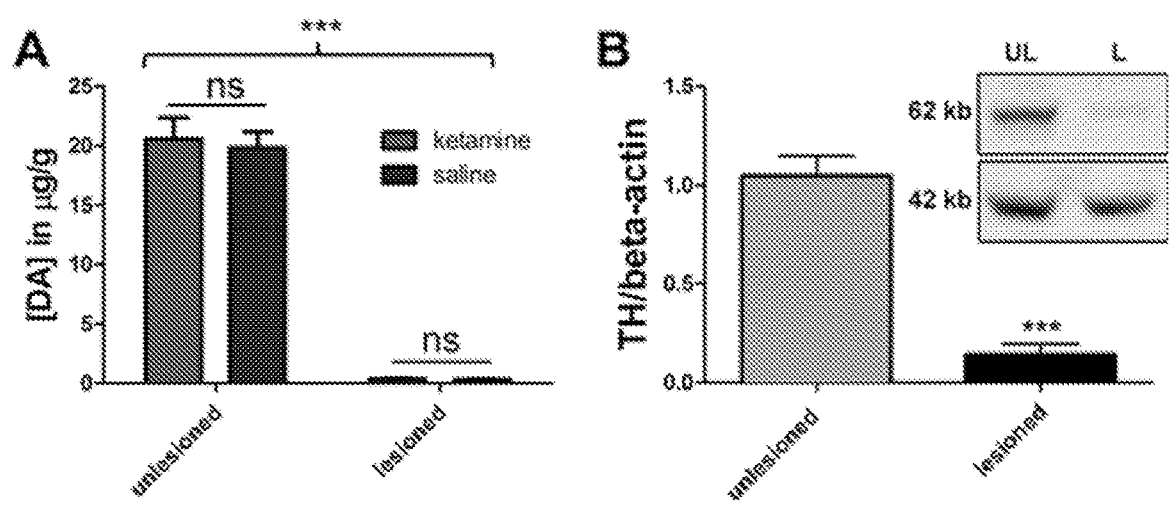
FIG. 2. Verification of unilateral 6-OHDA lesion. (A) Electrochemical detection of striatal DA content. The DA content (mean±SEM) is reduced by >95% in the lesioned side, and [DA] was unchanged by an acute i.p. injection of 20 mg/kg ketamine (n=7) vs. saline (n=5) 30 min before rats were euthanized, showing that there is no acute effect on overall striatal DA levels by ketamine in these animal with multiple prior exposures to ketamine (2 way ANOVA, Bonferroni post-hoc test). (B) Semi-quantitative western analysis of striatal tyrosine hydroxylase (TH) expression. TH was normalized to β-actin as internal standard, mean values±SEM are plotted, and expression is reduced by 87% in the lesioned side (n=15; two-tailed t test) verifying the severity of the lesion. The Inset shows example blots (UL=unlesioned, L=lesioned). Statistical significant differences are depicted by asterisks (***$p<0.001$; ns=non-significant) (see, Bartlett M J, et al., Neuroscience Letters 2016; 612:121-125).
Figure 3:
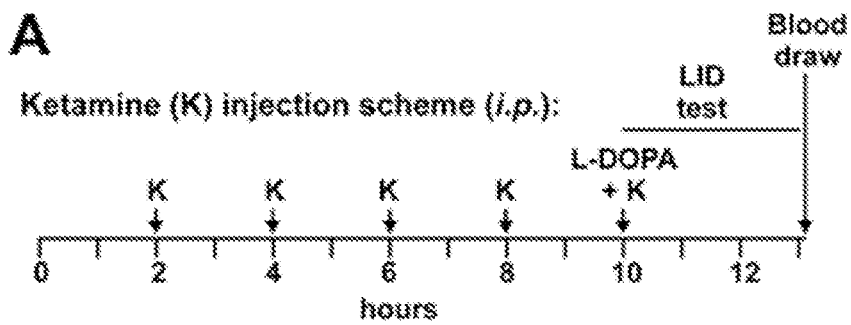
FIG. 3. Long-term dose-dependent reduction of LID after the low-dose-ketamine 'infusion' paradigm in the preclinical model. (A) Schematic of the 10 hour experimental protocol to mimic a ketamine infusion. (B) Severely dyskinetic LID rats (cohort #1) were tested with L-DOPA (7 mg/kg) every 3-4 days (white bars). The blue bars depict the days of ketamine challenges (K). The graph depicts mean limb, axial and orolingual (LAO)-AIMs±SEM; n=5; repeated measures ANOVAs vs. preceding baseline testing sessions; Tukey post-hoc tests; *$p<0.05$; $p<0.01$; *$p<0.005$). When comparing the pre-K (20 mg/kg) and the last testing session (blue line), a significantly reduced LAO-AIMs score remained, indicating a new stable lower level of LAO AIMs (*$p<0.05$; two tailed t test). (C) Ketamine 'infusion' did not have a significant effect on L-DOPA-induced contralateral locomotor scores in these animals and did not induce ipsilateral rotations in the presence of L-DOPA. (D) Acute low-dose-ketamine does not reduce LID. A separate cohort #2 of moderately dyskinetic LID rats was challenged with L-DOPA (5 mg/kg) every 3-4 days and AIMs were evaluated. The blue bars depict the days of acute ketamine (K; i.p.) challenges (mean LAO-AIMs±SEM; n=9; repeated measures ANOVAs vs. preceding baseline testing sessions; ns) (see, Bartlett M J, et al., Neuroscience Letters 2016; 612:121-125).
Figure 3:
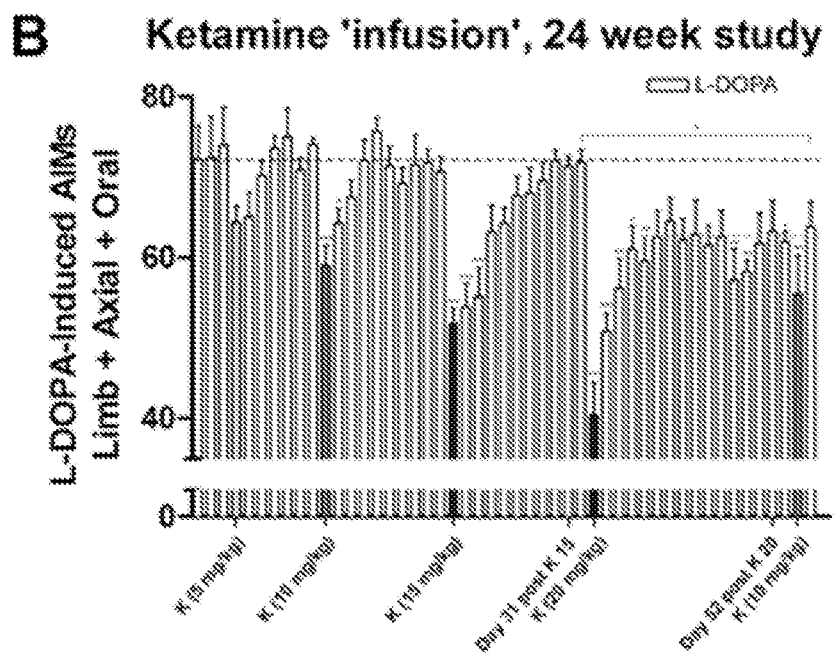
Figure 3:
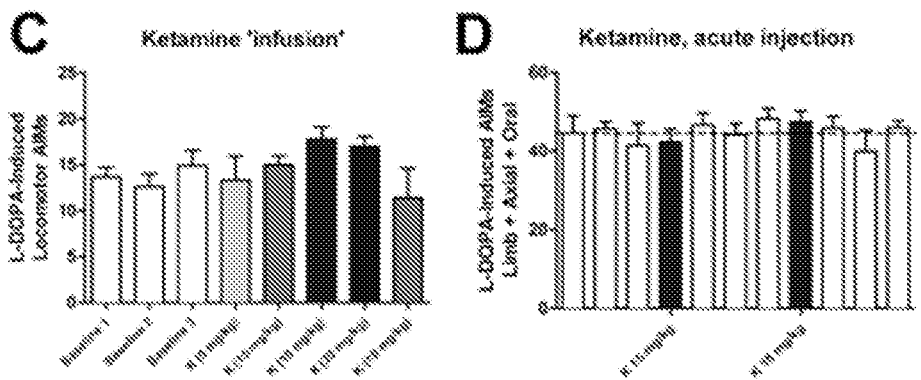

Preclinical Data:

Studies were conducted in the standard preclinical rat LID model (Dekundy et al., 2007). Verification for the unilateral lesion in both cohorts is shown in FIG. 2A, B. The rats in cohort #1 showed severe LID and a dose-dependent long-term anti-dyskinetic effect of low-dose ketamine when given for a 10 hr period was demonstrated (FIG. 3A,B); to mimic the patient infusion ketamine was injected 5×i.p. two hrs apart, 7 mg/kg L-DOPA was co-injected at the $5^{th}$ injection, and then the abnormal involuntary movements—(AIMs) scores were evaluated. This approach was used as it is not possible to use a regular infusion in a behaving rat and given the long-term nature of the experiment clogging of surgically inserted mini-pumps was a concern. After a 5 mg/kg ketamine-'infusion', there was a reduction of the AIMs score that lasted 7 days post-injection, before the baseline level (black dashed line) was reached again. After the 10 mg/kg ketamine-'infusion' it took 10 days before the baseline AIMs score was reached again and after the 15 mg/kg ketamine-'infusion', it took 31 days before the baseline AIMs score level was reached again. Most impressive, however, was the effect of 20 mg/kg ketamine-'infusion', which resulted in a persistent reduction of AIMs scores that lasted for at least 55 days post-injection, and what appeared to be a new lower stable AIMs level was established (blue dashed line). A 10 mg/kg ketamine-'infusion' was given after these treatments to test for sensitization resulting from ketamine treatment. No change in the already-reduced AIMs score was observed following this dosage, suggesting that reduced AIMs scores following the 20 mg/kg injection was not due to sensitization. At all the tested doses ketamine did not significantly change L-DOPA-induced contralateral locomotor behavior (FIG. 3C), and specifically did not acutely induce the ipsiversive turning behavior that is indicative of a worsening of the Parkinsonism in this model, as it has been shown by the non-competitive N-methyl-D-aspartate (NMDA) receptor antagonist MK-801 (Flores et al., 2014; Paquette et al., 2010). To investigate if the longer exposure to ketamine is necessary a separate cohort #2 of rats with moderate LID was tested to see if an acute ketamine injection would also be anti-dyskinetic (FIG. 3D). The rats were primed and tested with 5 mg/kg L-DOPA, and two acute i.p. injections of 15 mg/kg ketamine (fourteen days apart) did not lead to any change in the AIMs scores.

Example II

This example demonstrates that a low-dose sub-anesthetic racemic ketamine infusion once a week reduces the development of LID in a preclinical model. Unilaterally 6-hydroxydopamine (6-OHDA)-lesioned PD rats were injected daily with L-DOPA (days 0-13: 6 mg/kg; days 14-28: 12 mg/kg; i.p.) to induce dyskinesia and tested for limb, axial and oral (LAO) abnormal involuntary movements (AIMs) twice a week for 3 hours by blinded investigators.

Figure 4:
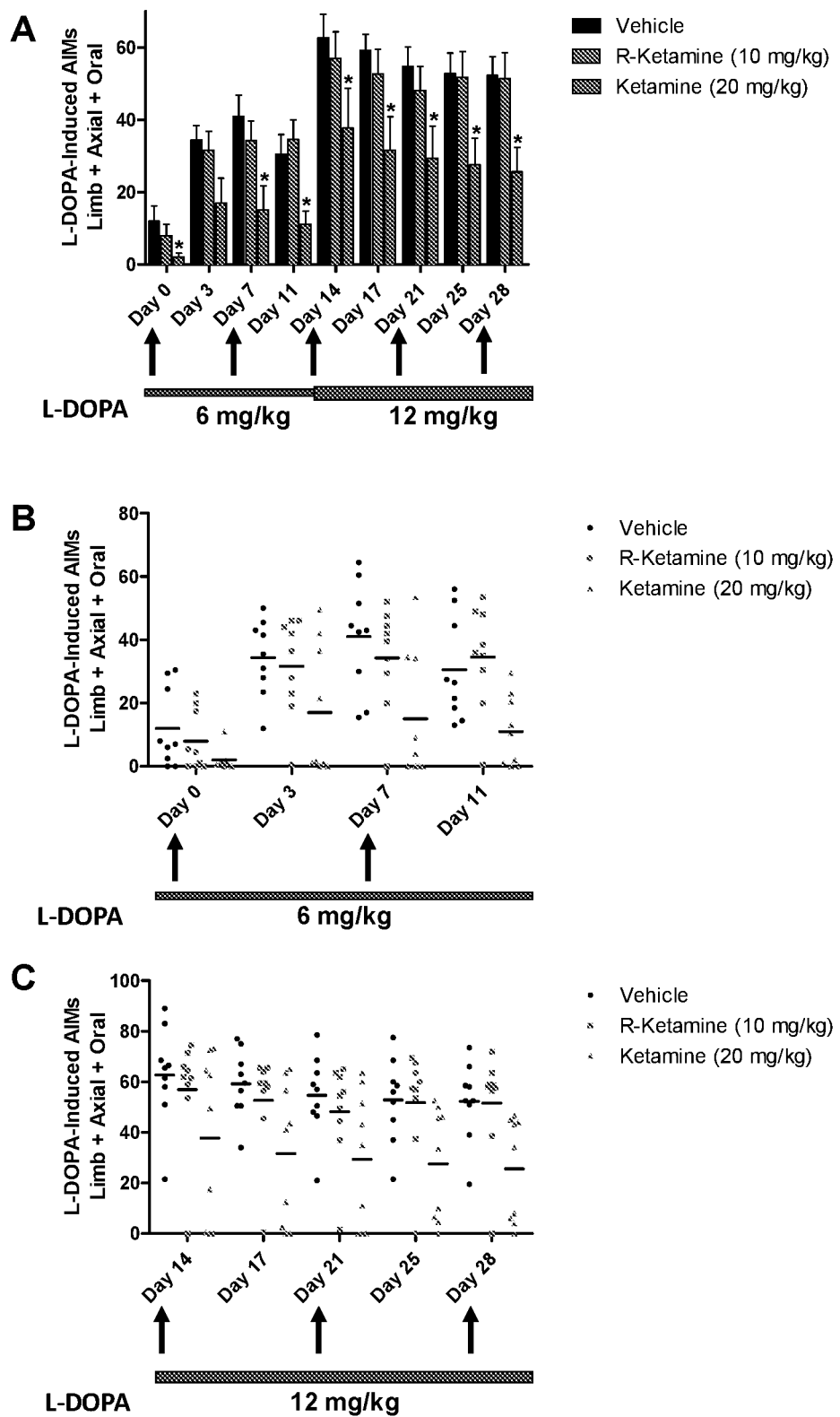
FIGS. 4A, B and C. Low-dose sub-anesthetic racemic ketamine infusion once a week reduces the development of LID in the preclinical model. Unilaterally 6-hydroxydopamine (6-OHDA)-lesioned PD rats were injected daily with L-DOPA (days 0-13: 6 mg/kg; days 14-28: 12 mg/kg; i.p.) to induce dyskinesia and tested for limb, axial and oral (LAO) abnormal involuntary movements (AIMs) twice a week for 3 hours by blinded investigators. In panel (A) the mean LAO AIMs scores±SEM are plotted showing a 50% reduction after racemic low-dose ketamine infusions. The black arrows point to the days of the 10-hours racemic ketamine, R-ketamine or vehicle infusion paradigm (n=9 per group, *p<0.05, ANOVAs, Tukey post hoc tests). The scatter plots depicting every animal separately in both the 6 mg/kg L-DOPA period in (B) and the 12 mg/kg L-DOPA period in (C) reveal that there are responders and non-responders in the racemic ketamine-treated group: 4 of 9 animals did not develop any dyskinesia or only very subtle dyskinesia, while only 1 in the R-ketamine-treated group, and none in the vehicle control group. The black lines depict the mean value per groups.

FIG. 4A shows the mean LAO AIMs scores±SEM are plotted showing a 50% reduction after racemic low-dose ketamine infusions. The black arrows point to the days of the 10-hours racemic ketamine, R-ketamine or vehicle infusion paradigm (n=9 per group, *p<0.05, ANOVAs, Tukey post hoc tests).

FIGS. 4B and 4C present scatter plots depicting every animal separately in both the 6 mg/kg L-DOPA period in (B) and the 12 mg/kg L-DOPA period in (C) reveal that there are responders and non-responders in the racemic ketamine-treated group: 4 of 9 animals did not develop any dyskinesia or only very subtle dyskinesia, while only 1 in the R-ketamine-treated group, and none in the vehicle control group. The black lines depict the mean value per groups.

This data indicates that racemic ketamine infusions reduces the development of dyskinesia and therefore is indicative for early use in the treatment of L-DOPA-induced dyskinesia.

Example III

This example describes the effects of racemic ketamine injection (20 mg/kg) on high-frequency (HFO) and beta band oscillations in the motor cortex (M1) and dorsolateral striatum (DLS).

Using the 10-hour racemic ketamine paradigm (5 i.p. injections every 2 hours), simultaneous local-field activity in multiple brain structures in two awake and behaving naïve rats was measured. Recordings were acquired from a 64 channel fixed electrode array. Average response across 2 animals and 5 sessions was obtained.

Figure 5:
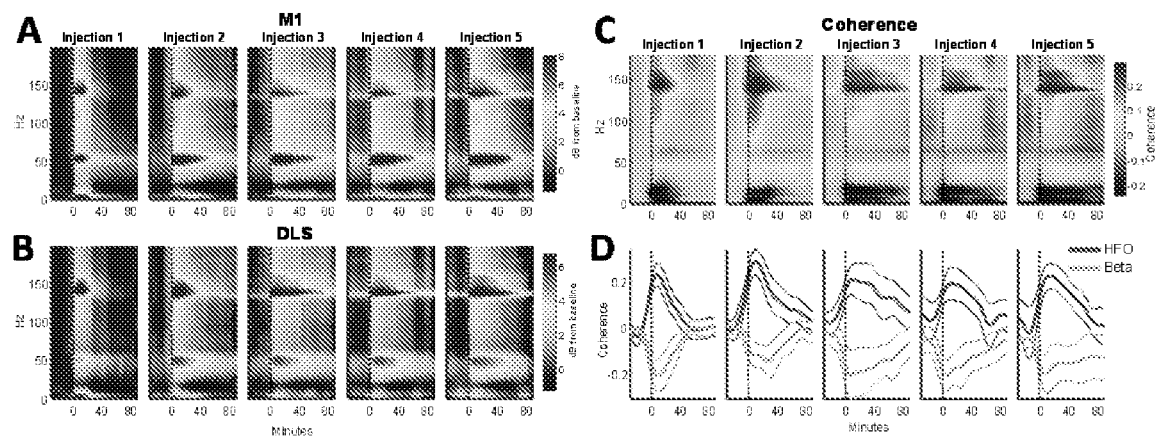
FIGS. 5A, B, C and D. Effects of racemic ketamine injection (20 mg/kg) on high-frequency (HFO) and beta band oscillations in the motor cortex (M1) and dorsolateral striatum (DLS). Using the 10-hour racemic ketamine paradigm (5 i.p. injections every 2 hours), we measured simultaneous local-field activity in multiple brain structures in two awake and behaving naïve rats. Recordings were acquired from a 64 channel fixed electrode array. Average response across 2 animals and 5 sessions. (A+B) Power spectrogram from a 10 hour session created by averaging spectra acquired from 5 recording sessions. Vertical lines indicate K injection times. A clear increase in high-frequency activity (120-140 Hz) was observed after each ketamine injection in both motor cortex (M1) and dorsolateral striatum (DLS). (C) Plot of mean coherence in all frequencies <200 Hz. Coherence in the HFO frequency band increased following each injection. (D) Plot of the mean coherence in the HFO and beta bands (n=5 sessions). Thin lines indicate SEM. Coherence in these two bands was anti-correlated (r=−0.65). Coherence in the HFO band appeared to increase with successive injections while coherence in the beta band decreased.

FIGS. 5A and B shows power spectrogram from a 10 hour session created by averaging spectra acquired from 5 recording sessions. Vertical lines indicate K injection times. A clear increase in high-frequency activity (120-140 Hz) was observed after each ketamine injection in both motor cortex (M1) and dorsolateral striatum (DLS).

FIG. 5C shows a plot of mean coherence in all frequencies <200 Hz. Coherence in the HFO frequency band increased following each injection.

FIG. 5D shows a plot of the mean coherence in the HFO and beta bands (n=5 sessions). Thin lines indicate SEM. Coherence in these two bands was anti-correlated (r=−0.65). Coherence in the HFO band appeared to increase with successive injections while coherence in the beta band decreased.

Accordingly, as decoupling of beta and gamma band activity in motor cortex is indicated as one of the mechanisms of action for deep brain stimulation (DBS) in the subthalamic nucleus to treat PD patients, these results demonstrate that low-dose ketamine infusions act as a 'chemical DBS'.

Example IV

This example describes the effects of racemic ketamine injection (20 mg/kg) on high-frequency (HFO), gamma and beta band oscillations in the motor cortex (M1) and dorsolateral striatum (DLS) of a rodent Parkinson's disease model.

Using a 10-hour racemic ketamine paradigm (5 i.p. injections every 2 hours), simultaneous measurement of local-field activity in multiple brain structures in three awake and behaving unilateral 6-hydroxydopamine (6-OHDA)-lesioned rats, a common model of Parkinson's disease. Recordings were acquired from a 64 channel fixed electrode array. Average response across 3 animals. Power spectrogram from a 10 hour session created by averaging spectra acquired. Vertical lines indicate ketamine injection times.

Figure 6:
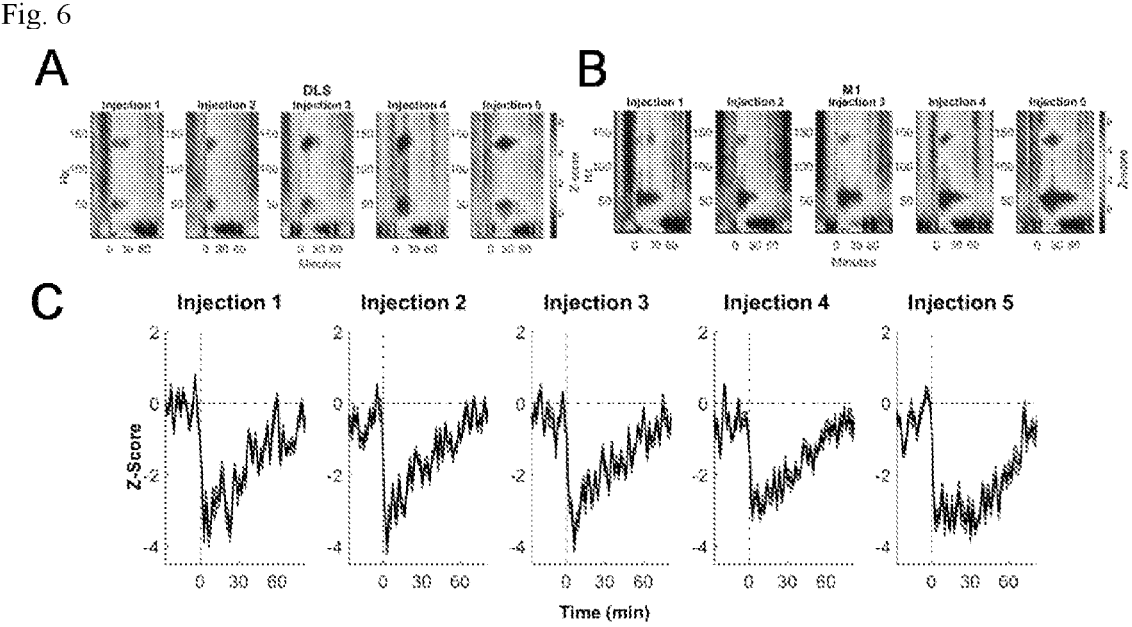
FIGS. 6A and B. Effects of racemic ketamine injection (20 mg/kg) on high-frequency (HFO), gamma and beta band oscillations in the motor cortex (M1) and dorsolateral striatum (DLS) of a rodent Parkinson's disease model. Using the 10-hour racemic ketamine paradigm (5 i.p. injections every 2 hours), we measured simultaneous local-field activity in multiple brain structures in three awake and behaving unilateral 6-hydroxydopamine (6-OHDA)-lesioned rats, a common model of Parkinson's disease. Recordings were acquired from a 64 channel fixed electrode array. Average response across 3 animals. Power spectrogram from a 10 hour session created by averaging spectra acquired. Vertical lines indicate ketamine injection times. A clear increase in high-frequency activity (120-140 Hz) and gamma band activity (40-60 Hz) was observed after each ketamine injection in both DLS (A) and M1 (B). Beta-Gamma cross-frequency coupling (CFC) in the DLS of 6-OHDA-lesioned PD animals is reduced following each ketamine injection (C). Units are in z-scores relative to baseline CFC during the 20 minutes prior to the first injection. Cross-frequency coupling measures the degree to which fluctuations in the power of the high-frequency oscillation (gamma) is correlated with the phase of the lower-frequency oscillation (beta). Error bars indicate SEM (n=15 sessions across 3 animals).

FIGS. 6A and B show a clear increase in high-frequency activity (120-140 Hz) and gamma band activity (40-60 Hz) was observed after each ketamine injection in both DLS (A) and M1 (B).

FIG. 6C shows beta-gamma cross-frequency coupling (CFC) in the DLS of 6-OHDA-lesioned PD animals is reduced following each ketamine injection. Units are in z-scores relative to baseline CFC during the 20 minutes prior to the first injection. Cross-frequency coupling measures the degree to which fluctuations in the power of the high-frequency oscillation (gamma) is correlated with the phase of the lower-frequency oscillation (beta). Error bars indicate SEM (n=15 sessions across 3 animals).

This data is in further support of the hypothesis that low-dose ketamine infusions act as a 'chemical DBS'.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes.

REFERENCES

1. Caixeta F V, Cornélio A M, Scheffer-Teixeira R, Ribeiro S, Tort A B L. Ketamine alters oscillatory coupling in the hippocampus. Sci Rep 2013; 3: 2348.
2. Dekundy A, Lundblad M, Danysz W, Cenci M A. Modulation of L-DOPA-induced abnormal involuntary movements by clinically tested compounds: further validation of the rat dyskinesia model. Behav. Brain Res 2007; 179: 76-89.
3. Diamond P R, Farmery A D, Atkinson S, Haldar J, Williams N, Cowen P J, et al. Ketamine infusions for treatment resistant depression: a series of 28 patients treated weekly or twice weekly in an ECT clinic. J Psychopharmacol 2014; 28: 536-544.
4. Feder A, Parides M K, Murrough J W, Perez A M, Morgan J E, Saxena S, et al. Efficacy of intravenous ketamine for treatment of chronic posttraumatic stress disorder: a randomized clinical trial. JAMA psychiatry 2014; 71: 681-688.
5. Flores A J, Bartlett M J, So L Y, Laude N D, Parent K L, Heien M L, et al. Differential effects of the NMDA receptor antagonist MK-801 on dopamine receptor D1- and D2-induced abnormal involuntary movements in a preclinical model. Neuroscience Letters 2014; 564: 48-52.
6. Hakami T, Jones N C, Tolmacheva E a, Gaudias J, Chaumont J, Salzberg M, et al. NMDA receptor hypofunction leads to generalized and persistent aberrant gamma oscillations independent of hyperlocomotion and the state of consciousness. PLoS One 2009; 4: e6755.
7. Hammond C, Bergman H, Brown P. Pathological synchronization in Parkinson's disease: networks, models and treatments. Trends in Neurosciences 2007; 30: 357-364.
8. Hille C J, Fox S H, Maneuf Y P, Crossman a R, Brotchie J M. Antiparkinsonian action of a delta opioid agonist in rodent and primate models of Parkinson's disease. Experimental Neurology 2001; 172: 189-198.
9. Hiyoshi T, Kambe D, Karasawa J I, Chaki S. Differential effects of NMDA receptor antagonists at lower and higher doses on basal gamma band oscillation power in rat cortical electroencephalograms. Neuropharmacology 2014; 85: 384-396.
10. Jenkinson N, Brown P. New insights into the relationship between dopamine, beta oscillations and motor function. Trends in Neurosciences 2011; 34: 611-618.
11. Koprich J B, Fox S H, Johnston T H, Goodman A, Le Bourdonnec B, Dolle R E, et al. The selective mu-opioid receptor antagonist ADL5510 reduces levodopa-induced dyskinesia without affecting antiparkinsonian action in MPTP-lesioned macaque model of Parkinson's disease. Mov Disord 2011; 26: 1225-1233.
12. Lapidus K A B, Levitch C F, Perez A M, Brallier J W, Parides M K, Soleimani L, et al. A Randomized Controlled Trial of Intranasal Ketamine in Major Depressive Disorder. Biol Psychiatry 2014; 76(12): 970-976.
13. Masimore B, Schmitzer-Torbert N C, Kakalios J, Redish A D. Transient striatal gamma local field potentials signal movement initiation in rats. Neuroreport 2005; 16: 2021-2024.
14. Murrough J W, Iosifescu D V, Chang L C, Al Jurdi R K, Green C E, Perez A M, et al. Antidepressant efficacy of ketamine in treatment-resistant major depression: A two-site randomized controlled trial. Am J Psychiatry 2013; 170: 1134-1142.
15. Murrough J W, Perez A M, Pillemer S, Stem J, Parides M K, Aan Het Rot M, et al. Rapid and longer-term antidepressant effects of repeated ketamine infusions in treatment-resistant major depression. Biol Psychiatry 2013; 74: 250-256.
16. Nicolás M J, López-Azcárate J, Valencia M, Alegre M, Pérez-Alcázar M, Iriarte J, et al. Ketamine-induced oscillations in the motor circuit of the rat basal ganglia. PLoS One 2011; 6: e21814.
17. Niesters M, Martini C, Dahan A. Ketamine for chronic pain: Risks and benefits. British J of Clinical Pharmacology 2014; 77: 357-367.
18. Olanow C W, Stem M B, Sethi K. The scientific and clinical basis for the treatment of Parkinson disease (2009). Neurology 2009; 72: S1-S136.
19. Pacheco D D F, Romero T R L, Duarte I D G. Central antinociception induced by ketamine is mediated by endogenous opioids and mu- And delta-opioid receptors. Brain Research 2014; 1562: 69-75.
20. Pan M, Tai C, Liu W, Pei J, Lai W, Kuo C. Deranged NMDAergic cortico-subthalamic transmission underlies parkinsonian motor deficits. J Clinical Investigation 2014; 124: 4629-4641.
21. Paquette M a, Anderson A M, Lewis J R, Meshul C K, Johnson S W, Paul Berger S. MK-801 inhibits L-DOPA-induced abnormal involuntary movements only at doses that worsen parkinsonism. Neuropharmacology 2010; 58: 1002-1008.
22. Pinault D. N-methyl d-aspartate receptor antagonists ketamine and MK-801 induce wake-related aberrant gamma oscillations in the rat neocortex. Biol Psychiatry 2008; 63: 730-735.
23. Razoux F, Garcia R, Léna I. Ketamine, at a dose that disrupts motor behavior and latent inhibition, enhances prefrontal cortex synaptic efficacy and glutamate release in the nucleus accumbens. Neuropsychopharmacology 2007; 32: 719-727.
24. Smith D J, Bouchal R L, deSanctis C A, Monroe P J, Amedro J B, Perrotti J M, et al. Properties of the interaction between ketamine and opiate binding sites in vivo and in vitro. Neuropharmacology 1987; 26: 1253-1260.

25. Wright J J, Goodnight P D, Mcevoy M D. The Utility of Ketamine for the Preoperative Management of a Patient with Parkinson's Disease. Anesth and Analg 2009; 108: 980-982.
26. Yue X, Falk T, Zuniga L a, Szabò L, Porreca F, Polt R, et al. Effects of the novel glycopeptide opioid agonist MMP-2200 in preclinical models of Parkinson's disease. Brain Research 2011; 1413: 72-83.
27. Yue X, Hariri D J, Caballero B, Zhang S, Bartlett M J, Kaut O, et al. Comparative study of the neurotrophic effects elicited by VEGF-B and GDNF in preclinical in vivo models of Parkinson's disease. Neuroscience 2014; 258: 385-400.

We claim:

1. A method of attenuating and/or treating a human patient suffering from levodopa induced dyskinesia, comprising administering to the patient two or more infusions within a ten-day period of a composition comprising a dose of ketamine or a pharmaceutically acceptable salt thereof to attenuate and/or ameliorate the symptoms of the levodopa induced dyskinesia,
   wherein the dose of ketamine or pharmaceutically acceptable salt thereof is about 0.15 mg/kg/hour to about 2 mg/kg/hour,
   wherein the duration of each infusion is approximately 60 minutes,
   wherein administering the composition results in the patient experiencing chemical-induced deep brain stimulation,
   wherein the chemical-induced deep brain stimulation results in attenuation and/or treating of the symptoms of the levodopa induced dyskinesia.

2. The method of claim 1, further comprising administration of carbidopa.

3. The method of claim 1, wherein the human subject is suffering from Parkinson's disease.

4. The method of claim 1, wherein the within a ten-day period is within 72 hours.

5. The method of claim 1, wherein ketamine is a metabolite of ketamine, wherein the metabolite of ketamine is selected from R-norketamine (NK), R-dehydronorketamine (DHK), S-norketamine (NK), S-dehydronorketamine (DHK), (2R,6R)-hydroxynorketamine (HNK), and (2S,6S)-hydroxynorketamine (HNK).

* * * * *